United States Patent [19]

Hort

[11] 4,119,790

[45] * Oct. 10, 1978

[54] LOW PRESSURE CATALYTIC ETHYNYLATION PROCESS

[75] Inventor: Eugene V. Hort, Wayne, N.J.

[73] Assignee: GAF Corporation, New York, N.Y.

[*] Notice: The portion of the term of this patent subsequent to Nov. 18, 1992, has been disclaimed.

[21] Appl. No.: 785,033

[22] Filed: Apr. 6, 1977

[51] Int. Cl.$^2$ ............................................. C07C 29/00
[52] U.S. Cl. .................................................. 568/855
[58] Field of Search .................................. 260/635 Y

[56] References Cited

U.S. PATENT DOCUMENTS 3,920,759  11/1975  Hort ................................. 260/635 Y Primary Examiner—Joseph E. Evans Attorney, Agent, or Firm—Walter C. Kehm; Walter Katz

[57] ABSTRACT

In accordance with the present invention, there is provided herein an improved low pressure, stirred, catalytic process by which butynediol can be produced continuously at a high rate of production, under safe conditions, and without simultaneously forming an excessive amount of undesirable by-products. The process of this invention can be carried out by heating acetylene and formaldehyde, at relatively low temperatures as compared to other processes using supported catalysts, in the presence of a stirred aqueous slurry of a finely-divided complex cuprous acetylide catalyst prepared from a precursor containing greater than 20% and less than 35% by weight of copper, and 0–3%, preferably 2–3%, by weight of bismuth, as the oxides, on a magnesium silicate carrier.

6 Claims, 2 Drawing Figures

FIG. I 4,119,790

LOW PRESSURE CATALYTIC ETHYNYLATION PROCESS

BACKGROUND OF THE DISCLOSURE

1. Field of the Invention

This invention relates to a low pressure catalytic ethynylation process for the production of butynediol, and, more particularly, it is concerned with an improved process which is characterized particularly by a high rate of production of butynediol.

2. Description of the Prior Art

Butynediol has been prepared in the past by an ethynylation reaction between acetylene and formaldehyde in the presence of a catalyst. Such processes are described, for example, in U.S. Pat. Nos. 2,232,867, 2,300,969, 2,487,069, 2,712,560, 2,768,215, 3,108,140, 3,294,849, 3,560,576 and 3,920,759. The low pressure, stirred ethynylation process using an aqueous slurry of a finely-divided catalyst of copper acetylide on a magnesium silicate carrier, described in U.S. Pat. No. 3,920,759, has represented a particularly significant advance in this field. This process provides butynediol at a reasonable rate under safe conditions. However, it would be advantageous to provide an improved method for producing butynediol by such a low pressure process.

Accordingly, it is an object of the present invention to provide an improved process for producing butynediol by a low pressure, stirred, catalytic ethynylation process at a high rate of production of butynediol, under safe conditions, and which affords a ready means of separating butynediol from catalyst in the reaction product effluent.

These and other objects and features of the invention will become apparent from the following more particular description of the invention.

SUMMARY OF THE INVENTION

In accordance with the present invention, there is provided herein an improved low pressure, stirred, catalytic process by which butynediol can be produced continuously at a high rate of production, under safe conditions, and without simultaneously forming an excessive amount of undesirable by-products. The process of this invention can be carried out by heating acetylene and formaldehyde, at relatively low temperatures as compared to other processes using supported catalysts, in the presence of a stirred aqueous slurry of a finely-divided complex cuprous acetylide catalyst prepared from a precursor containing greater than 20% and less than 35% by weight of copper, and 0-3%, preferably 2-3%, by weight of bismuth, as the oxides, on a magnesium silicate carrier.

The butynediol product thus is produced at a much higher rate than has heretofor been possible with a supported catalyst, and it can be rapidly and conveniently separated from the catalyst. The recovered catalyst slurry may be recycled to the reactor, with fresh formaldehyde feed, to provide continuous operation. Such continuous operation may be in a single vessel or a cascade of vessels. Butynediol solution which has been separated from the catalyst may be used for further operations.

The combination of high reaction rates at lower reaction temperatures and high catalyst separation rates provides increased productivity under otherwise similar reaction conditions, as compared to previous processes using supported catalysts, and this result is obtained without the increased catalyst sensitivity to detonation and decomposition characteristic of unsupported catalysts, and with a decrease in the amount of by-products produced.

DETAILED DESCRIPTION OF THE INVENTION

In the Drawings

Description of the Preferred Embodiments

Figure 1:
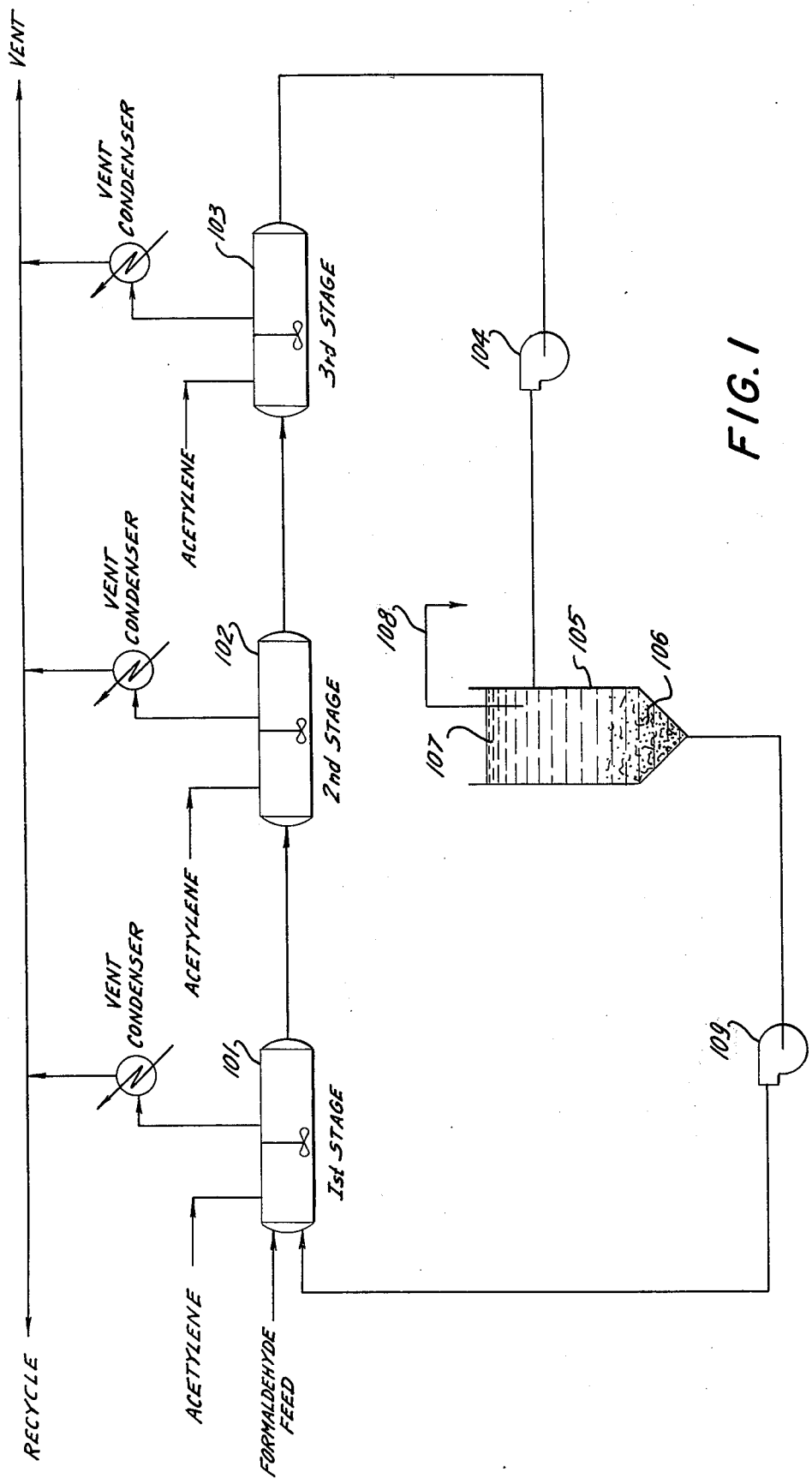
FIG. 1 is a schematic illustration of a continuous, low pressure ethynylation process for the production of butynediol in accordance with the teachings of the invention.

Referring now to FIG. 1, there is shown suitable apparatus for carrying out the continuous, low pressure ethynylation process of the invention. As mentioned, the ethynylation reaction per se comprises reacting formaldehyde with acetylene in the presence of an ethynylation catalyst. The reaction is carried out at low pressures, i.e. a partial pressure of acetylene of less than 2 atmospheres, and at a reaction temperature of about 80° C. to about 110° C., in a stirred, aqueous medium in the presence of the improved finely-divided complex cuprous acetylide ethynylation catalyst on a magnesium silicate support of the invention, which is present in the reaction mixture as a slurry.

The improved catalyst of the invention is a complex cuprous acetylide on a magnesium silicate carrier, which is generated in situ by reaction of cupric oxide with formaldehyde in the presence of acetylene, with preferably bismuth oxide, which oxide containing precursor material contains greater than 20% and less than 35% by weight of copper, and 0-3% by weight of bismuth, preferably 2-3%, of the total weight of precursor material, including carrier.

The ethynylation reaction may be conducted in several stages, usually with a series of connected reactors, preferably three in number, as shown, of approximately equal size. Each reactor is equipped with an efficient stirrer.

The reaction is commenced by pumping a suitable aqueous solution of formaldehyde, usually containing about 30–40% by weight formaldehyde, and admitting acetylene gas into the first reactor 101 containing the catalyst slurry at the prescribed temperature and pressure conditions. The reaction is continued to produce a reaction product which includes the desired butynediol. A small amount of propargyl alcohol usually formed as a by-product in the reaction is found also in the reaction product.

The reaction product then is continuously withdrawn from reactor 101 as a reaction product effluent which includes the catalyst slurry, and passed into reactor 102 (which is equivalent to a second stage). Further acetylene is introduced into the reaction product effluent obtained from reactor 101 to give a second effluent stream, which is then passed into reactor 103 (third stage). Meanwhile, the volatile matter passing upwards through the vent condensers can, optionally, either be vented to the atmosphere, or, preferably, recycled.

The reaction product effluent from the third stage or reactor 103 then is passed via pump 104 to the settling tank 105. Thereupon, the catalyst quickly settles to the bottom of vessel 105 as a concentrated catalyst slurry 106, leaving a clear liquid 107 above which contains the desired butynediol, together with small amounts of propargyl alcohol by-product, and unreacted acetylene and formaldehyde.

The liquid 107 then is removed as a product stream 108. The concentrated catalyst slurry 106 is recycled by means of pump 109 to the first reactor 101, thus providing a continuous process.

The improvement in the overall process attained herein arises from the high rate of production of butynediol and also by the rapid separation rates of aqueous effluent of butynediol and catalyst into a catalyst-free liquid and concentrated catalyst slurry, as compared to previous processes using different catalysts.

Figure 2:
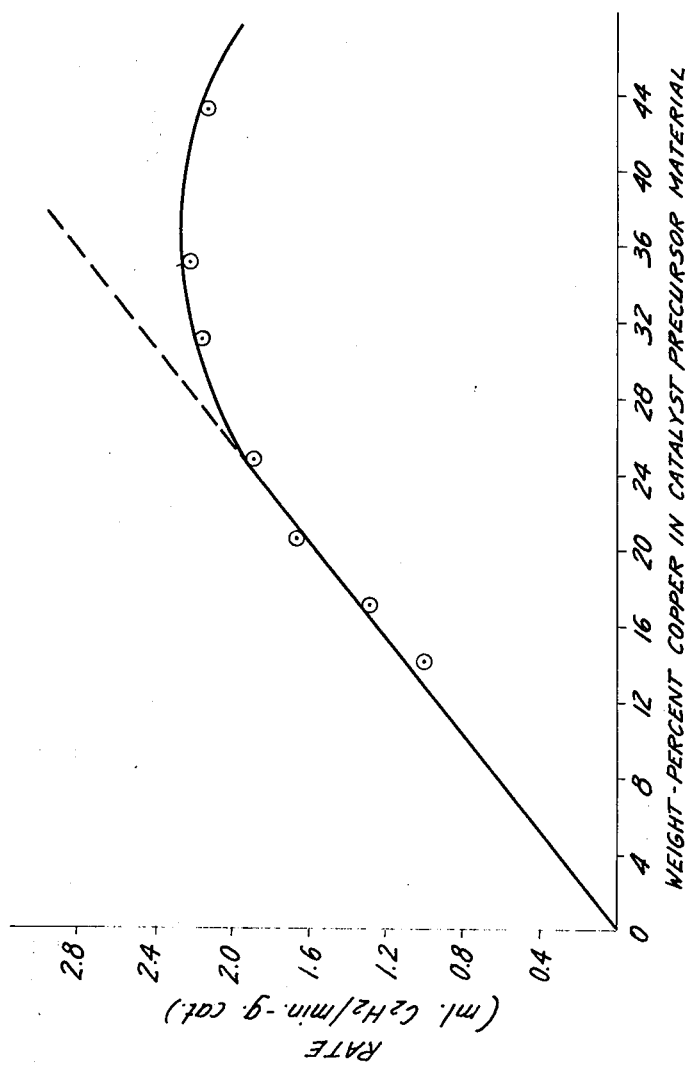
FIG. 2 is a graph of acetylene uptake rates vs. percent copper in the catalyst precursor for both the catalyst of the invention and for prior art catalysts.

FIG. 2 shows the effect of copper content in the catalyst precursor on the rate of production of butynediol in the process. The graph is plotted in acetylene uptake per minute per gram of catalyst used, which is proportional to the rate of butynediol produced, versus percent copper, for both the catalyst of this invention and for prior art copper catalysts. Under the same reaction conditions, it is seen that the reaction rate is increased substantially at a copper content greater than 20% by weight, and reaches a maximum at about 35% by weight of copper. At still higher copper concentrations, the rate declines appreciably. Significantly, doubling the copper content of the catalyst precursor from 13 to 26% effectively doubles the catalyst activity, when measured at about the same total acetylene uptake for each run.

While the reason for this rate effect with increased copper in this particular system, namely a low pressure, stirred, finely-divided, supported catalyst system, is not completely understood at present, it is indeed surprising, since it is known from work in the high pressure, fixed-bed, pelleted catalyst system, that increasing the amount of copper in the catalyst has virtually no effect on catalyst activity.

As a result of the high rates of production of butynediol achieved herein using the improved catalyst of the invention, other reaction parameters may be adjusted, if desired, to provide a purer butynediol product, and to decrease catalyst degradation. The most important process parameter which can be adjusted is the reaction temperature. In the process of this invention, the reaction may be run at a temperature lower than that used previously with catalysts of lesser activity, thereby assuring that the catalyst will not degrade as rapidly, and that less by-products will be formed. In general, the process of this invention may be carried out about 10°–15° C. lower than similar processes, for example, as described in U.S. Pat. No. 3,920,759, which uses a lower copper content catalyst, and still give comparable rates of production of butynediol. Of course, the process may be run at the same temperature as in the past, and if so, it will provide substantially higher rates. Suitably, the process of this invention may be run at the relatively low temperatures of about 80°–105°, and preferably at 90°–100°, which provides a high rate of production of butynediol with a minimum of by-products and catalyst degradation.

GENERAL PROCEDURES AND CONDITIONS OF THE ETHYNYLATION PROCESS

Preparation of Catalyst Precursor Material

The catalyst precursor material is prepared by impregnating magnesium silicate carrier with solutions of the metal salts. The magnesium silicate carrier has a bulk density of about 0.2 to 1.0 g./cm.$^2$ in powder form, and is impregnated with a solution of a cupric salt, and, preferably, also a bismuth salt, such as the nitrates thereof. The impregnated catalyst is heated to drive off volatiles, and then roasted, to convert the cupric and bismuth salts to the magnesium silicate-supported cupric oxide and bismuth oxide precursor of the active catalyst. Most of this precursor material will pass through a sieve having from 10 to 300 holes per inch.

Generation of Active Catalyst

The active catalyst itself is generated continuously in situ by introducing acetylene into a mixture of the catalyst precursor material and formaldehyde. Thereupon the cupric oxide is subjected to the simultaneous action of the reactants at the reaction temperature and pressure in a substantially aqueous medium. The catalyst generation reaction is preferably continued until the cupric copper is substantially completely converted to cuprous copper form, which, with the preferred cupric precursors, generally requires 4 to 48 hours after all the precursor has been contacted under the prescribed conditions. Preferably, also, the prescribed ethynylation reaction conditions of temperature, pH and acetylene/formaldehyde concentration balance and range, as will be described hereinafter, will be maintained throughout the catalyst generation. However, departures from the prescribed conditions during the course of the preparation reaction can be tolerated, as the reaction is relatively insensitive to minor changes in operating conditions.

During a continuous operation, it may be advantageous to add small amounts of catalyst on a continuous or incremental basis. This catalyst then generates without interrupting production.

In carrying out the catalyst generation, nitrogen or another substantially inert gas, such as methane or carbon dioxide, may be present, as may also the common components of crude acetylene, such as methylacetylene and ethylene. Oxygen is preferably excluded for safety reasons. In small catalyst batches, the supported cupric precursor may be slurried in cold neutral formaldehyde solution and the acetylene introduced while the slurry is heated. For larger batches, it may be preferable to introduce the cupric precursor incrementally to a hot neutral formaldehyde solution under acetylene pressure. The aqueous solution advantageously may be a stream containing propargyl alcohol and/or butynediol, e.g., a recycle stream.

Pressure

The ethynylation reaction is run at a pressure of less than 2 atmospheres. The acetylene partial pressure above the aqueous medium will be in the range of 0.1 to 1.9 atmospheres, and preferably about 0.4 to 1.5 atmospheres. For the purpose of the present invention, in the substantial absence of extraneous gas, the acetylene partial pressure may be taken as the total pressure minus the absolute pressure of water and formaldehyde at the reaction temperature. As in the catalyst generation, crude acetylene may be used, but for safety reasons, it should be substantially free of oxygen.

Formaldehyde Concentration

The formaldehyde concentration in the liquid medium in contact with the slurried catalyst in the course of the ethynylation reaction ordinarily will be from 0.1 to 60% and, advantageously, at least 0.3, and preferably 0.4 to 40%, at the outset of the reaction.

Catalyst Concentration

The catalyst will be present in amounts of about 1 to 20, preferably about 10, parts by weight of the aqueous medium.

pH

The pH of the aqueous medium is ordinarily in the range of 3 to 10, and preferably 5 to 6, and may be maintained by ion exchange of continuous feed, or by addition of a suitable buffering agent.

The pH of the aqueous medium normally decreases as the reaction proceeds due to formation of formic acid by disproportionation of formaldehyde. The rate and extent of the decrease in pH tends to increase with the initial acidity of the reaction medium, and also with temperature. Accordingly, the pH may be, and advantageously is, controlled to some extent by beginning at the preferred initial pH of 3 to 10, and particularly herein, by operating in the preferred low temperature range of about 90°–100° C. Additional control may be achieved, by adding small amounts of acid acceptor, such as sodium acetate, as the reaction proceeds. Further control may be achieved by carrying out the catalyst generation as a continuous stirred reaction, fresh neutral formaldehyde solution being continuously introduced into an agitated reaction zone, (any acidic effluent may, if desired, be filtered away from the copper-containing particles) as the reaction proceeds, all the while maintaining the acetylene partial pressure.

Recovery of Butynediol

The liquid from the catalyst separation may be heated and/or subjected to reduced pressure to volatilize formaldehyde, propargyl alcohol and a portion of the water which are condensed and combined with supplemental concentrated formaldehyde for recycle to the ethynylation reactor, purging any build up of methanol at convenient intervals in a continuous operation, and leaving the balance of the liquid as aqueous butynediol.

The following Examples will illustrate the invention.

EXAMPLE 1

Reaction Rate Data

Precursor catalysts of various copper concentrations were prepared by impregnating magnesium silicate with solutions of cupric nitrate and bismuth nitrate containing differing amounts of the salts. Accordingly, to prepare the 24.9% by weight copper catalyst, for example, 880 g. of $Cu(NO_3)_2.3H_2O$, 54 g. of $Bi(NO_3)_2.5H_2O$ and 75 g. of conc. nitric acid were diluted to 825 ml. and 100 ml. of the resultant impregnating solution was added to 100 g. of magnesium silicate powder (Phila. Quartz Co., Custom B-20).

The impregnated catalyst was dried at 120°–140° C. and roasted at 500° C. for 6 hrs. All roasted material passed through a 20 mesh sieve. Then 5 grams of the resultant catalyst material was mixed with 540 ml. of 35% formaldehyde solution and acetylene was introduced for 1–3 days until the acetylene uptake ceased. The catalyst slurry thus-generated was decanted and the decanted liquid filtered. The liquid was replaced with 500 ml. of a 10% formaldehyde solution. A buffer salt in the amount of 2.5 g. of sodium acetate (0.5%) was added giving a pH of 5.

The slurry was heated to 80° C. and acetylene then was introduced at a total pressure of 1 atm. The acetylene uptake was measured while stirring at 80°. After approximately 4 liters of acetylene had been consumed, the run was cooled below 40° C. and allowed to settle. The supernatant liquid was drawn off and replaced with a fresh 500 ml. aliquot of the buffered formaldehyde. For the fourth aliquot, the rate was calculated for comparison of different catalyst. The data obtained is presented below in Table I.

TABLE I

| % Cu | % Bi | Rate (vol. $C_2H_2$/min-g. of cat.) |
|---|---|---|
| 14.3 | 3.5 | 1.0 |
| 16.9 | 2.4 | 1.3 |
| 20.5 | 2.5 | 1.7 |
| 24.9 | 2.5 | 1.9 |
| 31.0 | 2.8 | 2.2 |
| 35.1 | 2.3 | 2.3 |
| 42.9 | 2.7 | 2.1 |

The data in Table I is plotted and shown in the graph of FIG. 2. As described previously, it demonstrates the significantly increased rate of production of butynediol with a copper contents in the catalyst precursor greater than 20% and less than 35% by weight.

EXAMPLE 2

Settling Rate Data

The settling rate of a generated 24.9% copper catalyst was compared to a 14.2% copper catalyst, each prepared as in Example 1, except that the catalyst charge was 20 g. instead of 5 g. Accordingly, 500 ml. of each generated catalyst slurry in Example 1 was placed in a graduated cylinder, stirred vigorously, and observed periodically. The results are shown in Table II below.

TABLE II

| Time Lapsed After Stirring of Slurry | Solid Level | |
|---|---|---|
| | 24.9% Cu Cat. | 14.2% Cu Cat. |
| 15 mins. | 40 ml. | 110 ml. |
| 35 mins | 35 ml. | 70 ml. |
| 16 hrs. | 30 ml. | 50 ml. |

The data shows that the 24.9% Cu catalyst settled much more rapidly, and to a more fully compacted bed, than the 14 2% Cu catalyst. Further it occupied only about 60% of the volume occupied by the low Cu catalyst.

EXAMPLE 3

Filtration Rates

Filtration rates were measured on 500 ml. of reaction product slurries, and also on 500 ml. water slurries, of both generated catalysts. The filtrations were carried out using a vacuum of 35–40 mm Hg and a Buchner funnel fitted with a Coors #1 5.5 cms. ID and Whatman #4 filter paper.

TABLE III

|  | 24.9% Cu Cat. | 14.2% Cu Cat. |
| --- | --- | --- |
| Filtration times of 500 ml. of reaction solution-catalyst slurries | 21 min. | 60 min. |
| Filtration times of 500 ml. of water-catalyst slurries | 8 min. | 28 min. |

The data in Table III demonstrate that for the higher copper catalyst, there is a considerable improvement in the filtration rate. The catalyst of 24.9% copper filtered from both a product slurry and a water slurry in about one-third the time needed for corresponding filtrations with a catalyst of 14.2% copper.

EXAMPLE 4

Shock Tests

Catalysts having 22.7%, 24.9% and 35.1% copper were tested after use for shock sensitivity after drying en vacuo by striking small portions of each with a hammer on a solid bench top. No sparking or detonation was observed. The catalysts sparked only mildly when held in a Bunsen burner flame.

EXAMPLE 5

Comparative Rate Data for a Continuous Ethynylation Using Different Catalysts 11 kg. of a catalyst (10% of charge) of 22.7% by weight copper and 2.3% by weight bismuth on a magnesium silicate support was slurried into a reactor, charged with 100 liters of 20% formaldehyde at a pH of 5.2. Acetylene was introduced at 2-15 psi and the temperature raised to 95° C. The run was continued in batch fashion for 8 hrs. and then run in continuous fashion. The yield of butynediol product was observed to be more than 60% greater than in a comparable run using the same weight of a 12% copper catalyst.

A similar comparison was made by running the ethynylation reaction with the low copper catalyst at a reaction temperature 10° C. higher than for the high copper catalyst, i.e. at 105° C. instead of 95° C. The low copper was still 20% slower and gave a less pure butynediol product.

While the invention has been described with particular reference to certain embodiments thereof, it will be understood that certain modifications and changes may be made which are within the skill of the art. Therefore it is intended to be bound only by the appended claims.

What is claimed is:

1. An improved low pressure catalytic ethynylation process for producing butynediol at a high rate of production, safely, and without forming an excessive amount of undesirable by-products, which comprises: reacting formaldehyde and acetylene at a partial pressure of acetylene of less than about 2 atmospheres, in an aqueous medium, under agitation, at a reaction temperature of about 80°-105° C., in the presence of an ethynylation catalyst slurry consisting essentially of a water-insoluble complex cuprous acetylide powder generated from a catalyst precursor material containing greater than 20% and less than 35% by weight of copper, 0 to about 3% by weight of bismuth, and a magnesium silicate carrier therefor.

2. A process according to claim 1 wherein said reaction is carried out continuously.

3. A process according to claim 1 wherein said reaction temperature is about 90°-100° C.

4. A process according to claim 1 wherein said catalyst precursor material contains about 2% to about 3% bismuth.

5. An improved, continuous, low pressure, catalytic ethynylation process for producing butynediol at a high rate, safely, and without forming an excessive amount of undesirable by-products, which comprises:
 (a) continuously reacting formaldehyde and acetylene in a reaction zone at a partial pressure of acetylene of less than about 2 atmospheres, in an aqueous medium, under agitation, at a reaction temperature of about 80°-105° C., in the presence of an ethynylation catalyst slurry consisting essentially of a water-insoluble cuprous acetylide powder made from a catalyst precursor material containing greater than 20% and less than 35% by weight of copper, 0 to about 3% by weight of bismuth, on a magnesium silicate carrier therefor, to produce thereby a reaction product containing butynediol,
 (b) continuously withdrawing said reaction product and said catalyst slurry as an effluent by settling,
 (c) separating said effluent into a catalyst-free liquid containing said butynediol, and a concentrated catalyst slurry, and
 (d) continuously recycling said concentrated catalyst slurry to said reaction zone.

6. A continuous, multi-stage, low pressure ethynylation process for the production of butynediol which comprises:
 (a) continuously reacting formaldehyde and acetylene in a first stage reaction zone at a partial pressure of acetylene of less than 2 atmospheres and a reaction temperature of about 80° to about 105° C., in a stirred aqueous medium, in the presence of an ethynylation catalyst slurry consisting essentially of a finely-divided water-insoluble complex cuprous acetylide powder made from a catalyst precursor material containing greater than 20% and less than 35% by weight of copper, 0 to about 3% by weight of bismuth on a magnesium silicate carrier therefor, to form a first stage reaction product containing butynediol,
 (b) continuously withdrawing said first stage reaction product and said catalyst slurry as a first stage effluent,
 (c) continuously passing said first stage effluent into a second stage reaction zone into which additional acetylene is being supplied,
 (d) repeating steps (b) and (c), if desired, to other additional stage reaction zones to produce a final stage effluent,
 (e) continuously withdrawing said final stage effluent,
 (f) continuously separating said final stage effluent by settling into catalyst-free liquid containing said butynediol and a concentrated catalyst slurry, and,
 (g) continuously recycling said concentrated catalyst slurry to said first reaction zone.

* * * * *